(12) United States Patent
Werenskiold et al.

(10) Patent No.: US 6,528,493 B2
(45) Date of Patent: *Mar. 4, 2003

(54) SCREENING METHODS FOR IDENTIFYING MODULATORS OF PROLIFERATION AND DIFFERENTIATION OF BONE CELLS

(75) Inventors: Anne Katrin Werenskiold, Munich (DE); Jörg Schmidt, Munich (DE)

(73) Assignee: GSF-Forschungzentrum fur Umwelt und Gesundheit, GmbH, Neuherberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/045,585

(22) Filed: Mar. 20, 1998

(65) Prior Publication Data

US 2001/0011127 A1 Aug. 2, 2001

(51) Int. Cl.⁷ .................. A01N 45/00; A61K 31/70; A61K 39/395; G01N 33/566; C07H 21/04
(52) U.S. Cl. .................. 514/44; 435/7.1; 435/7.2; 435/69.5; 435/252.3; 435/320.1; 436/501; 424/130.1; 424/139.1; 424/141.1; 424/143.1; 530/350; 530/351; 530/387.1; 530/387.9; 530/388.22
(58) Field of Search .................. 530/350, 351, 530/388.22, 387.1, 387.9; 435/7.1, 7.2, 69.5, 252.3, 320.1; 436/501; 424/130.1, 139.1, 141.1, 143.1; 514/44

(56) References Cited

PUBLICATIONS

Werenskiold, AK et al., Cell Growth and Differentiation 6(171–177)1995, Feb. 1995.*
Werenskiold, AK et al., Laboratory Investigation 79(529–536)1999, May 1999.*
Moritz, D.R., et al Hybridoma 17(107116)1998, Nov. 1998.*
Gayle et al J. Biol. Chem. 271(5784)96, 1996.*
Kumar et al., J. Biol. Chem. 270(27905)95, 1996.*
Casser–Bette, M., et al., 1990, Calcif. Tissue Int., 46: 46–56.
Chirgwin, J.M. et al., 1979, Biochemistry, 18: 5294–5299.
Chu, M.L., et al. 1982, Nuc. Acids Res., 10:5925–5934.
Fort, P., et al. 1985, Nuc. Acids Res., 13:327–334.
Gayle, M.A., et al. 1996, J. Biol. Chem. 271:5784–5789.
Jaggi, R., et al. 1986, EMBO J 5: 2609–2616.
Klemenz, R., et al. 1989, Proc. NatL Acad. Sci. USA, 86:5708–5712.
Kumar, S., et al. 1995, J. Biol. Chem., 270:27905–27913.
Owen, T.A., et al. 1990, J. Cell. Physiol., 143: 420–430.
Owen, T.A., et al. 1993, Proc. NatL Acad. Sci. USA, 90:1503–1507.
Rössler, U., et al., 1995, Dev. Biol, 168:86–97.
Rupp, B., et al. 1995, Biochem. Biophys.Res. Corn., 216:595–601.
Schmidt, J., et al. 1988, Differentiation, 39:151–160.
Schüle, R., et al. 1990, Cell, 61:497–504.
Stosiv–Gruyiy et al., 1995, Journal of Chemotherapy 7:67–70.
Thomassen, E., et al. 1995, Cell Growth Differ., 6:178–184.
Tominaga, S., et al. 1992, Biochim. Biophys. Acta, 1171:215–218.
Trüb, T., et al. 1994, Proc. Nati. Acad. Sci. USA, 91:3896–3900.
Weiss, M.J., et al 1986, Proc. Natl. Acad. Sci. USA, 83:7182–7186.
Werenskiold, A.K., et al. 1995, Cell Growth Differ., 6:171–177.
Werenskiold, A.K. 1992, Eur. J. Biochem., 204:1041–1047.
Yanagisawa, K., et al. 1993, FEBS Lett., 318:83–87.
Yanagisawa et al., 1992, FEBS Letters 302:51–53.
Werenskiold et al., 1999, Laboratory Investigation 79:529–536.

* cited by examiner

*Primary Examiner*—Yvonne Eyler
*Assistant Examiner*—Michael Brannock
(74) *Attorney, Agent, or Firm*—Akin, Gump, Strauss, Hauer & Feld, L.L.P.

(57) ABSTRACT

The present application relates to a compositions comprising a compound which modulates the activity of T1-M protein, the use of compounds which modulate the activity of T1-M protein, and an in vitro method for influencing the proliferation and/or differentiation potential of bone cells.

10 Claims, 7 Drawing Sheets

T1-antisense RNA inhibits T1 expression

T1-antisense inhibits osteogenic differentiation

K12

K12-S2

K12-AS3

Expression of T1 and osteocalcin mRNA in K12 tumors

Gene expression in 3D cultures of K12 and MC3T3 cells

MODEL OF THE FUNCTION OF T1-M PROTEIN

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:  PCR Primer
<220> FEATURE:

<400> SEQUENCE: 1
cgatctagaa gtaaatcgtc ctggggtc                                              28

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence:  PCR Primer
<220> FEATURE:

<400> SEQUENCE: 2
cgggatcccg ggcagatcta agctttgtga atgatctggt ggc                             43
```

SCREENING METHODS FOR IDENTIFYING MODULATORS OF PROLIFERATION AND DIFFERENTIATION OF BONE CELLS

CROSS REFERENCE TO RELATED APPLICATIONS

The present application claims priority under 35 U.S.C. §119(a) to German Priority Document No. 197 11 933.6, filed on Mar. 21, 1997.

FIELD OF THE INVENTION

The field of the invention is compounds which affect proliferation and differentiation of bone cells.

BACKGROUND OF THE INVENTION

Bone differentiation is a complex process that involves the proliferation of osteoblasts and the formation of bone matrix. During childhood, a pronounced remodeling of bone takes place to allow skeletal growth, and remodeling continues throughout life. A controlled balance of bone destruction and new bone formation is essential for the maintenance of a specific bone mass. A reduced ability to produce new bone results in an overall loss of bone mass, osteoporosis, which represents a major medical problem, in particular, for post-menopausal women.

Osteogenesis in vivo and in various tissue culture systems may be separated into three consecutive stages. The early proliferation stage is characterized by DNA synthesis and the expression of genes, the gene products of which play a role in the formation of extracellular matrix, including collagen type 1, fibronectin and TGF-$\beta$. The second stage of matrix maturation is characterized by a high expression of alkaline phosphatase which may condition the osteoid matrix for the third stage, characterized by synthesis of osteocalcin.

Processes of bone differentiation are mediated by a large number of growth factors and cytokines, many of which accumulate in calcified bone matrix. A key event controlling the extent of new bone formation is the transition of proliferating osteoblasts to resting bone cells which deposit bone matrix. The signals inducing this maturation process have not been identified up to now and are vaguely designated as factors involved in bone matrix maturation. Knowledge of such factors would make it possible to reduce or even entirely inhibit osteopetrotic growth or, inversely, stimulate proliferation of preosteoblasts, e.g., to attenuate osteoporotic symptoms.

T1-M is a receptor closely related to interleukin-1 (IL-1) receptor, but lacking affinity for IL-1 ligand. Up to now, the ligand binding to T1-M has not exactly been known, but two possible ligands have recently been described (Kumar, 1995; Gayle, 1996). The biological functions of these ligands remain to be elucidated. The receptor T1-M is always membrane-associated and is constitutively present on hematopoietic cells of the erythroid and mast cell lineages. It represents 2–5% of the total T1 protein produced (T1:T1-M and T1-S). By contrast, an extracellular soluble variant, the ligand binding domain of the complete T1-M receptor, T1-S, is secreted to the environment.

However, T1-S, is not a cleavage product of T1-M, but is expressed by differential splicing of T1 RNA in differentiating tissues, including bones and mammary glands. T1-S represents about 95% of the produced T1 protein; it is deposited in newly formed bone matrix. The T1-S and T1-M proteins as well as the gene coding for the two proteins have been described in detail in Klemenz (1989), Yanagisawa (1993) and Thomassen (1995) for mouse and in Tominaga (1992) for the human protein. Each of these references is hereby incorporated by reference herein.

There is a long felt need for the identification and development of agents which affect the proliferation and differentiation of bone cells. The present invention satisfies this need.

SUMMARY OF THE INVENTION

The invention relates to a composition comprising a compound capable of directly or indirectly modulating the activity of endogenous T1-M protein, the compound optionally containing one or more physiologically compatible additives.

In one aspect, the compound influences the activity of the T1-M protein by modulating the expression thereof.

In another aspect, the compound influences the activity of the T1-M protein by interacting with the T1-M protein.

In yet another aspect, the compound is capable of reducing the activity of the T1-M protein.

In a further aspect, the compound is a T1-M antisense nucleic acid. IN a preferred embodiment, the antisense nucleic acid is complementary to a portion of T1-M mRNA. In another preferred embodiment, the antisense nucleic acid is complementary to the 5' region of T1-M ORF. In yet another preferred embodiment, the antisense nucleic acid is a DNA oligonucleotide having a sequence complementary to a DNA sequence selected from nucleotides 191–1201 and 277–796 of the cDNA sequence of T1-M ORF.

In another aspect, the compound is a T1-S-sense nucleic acid. In a preferred embodiment, compound is a T1-S mRNA.

In yet another aspect, the compound is an inhibitor which inhibits the function of the T1-M protein. In a preferred embodiment, the inhibitor is selected from the group consisting of a monoclonal antibody, a polyclonal antibody and a fragment of an antibody.

In a further aspect, the compound influences the activity of the T1-M protein by binding a T1-M protein ligand.

In another aspect, the compound is an expression vector which is capable of expressing T1-S. In a preferred embodiment, the compound is a competitive inhibitor of T1-M protein ligand binding. In another preferred embodiment, the competitive inhibitor is T1-S protein.

In yet another aspect, the compound enhances the activity of the T1-M protein. In a preferred embodiment, the compound is an expression vector capable of expressing T1-M. In yet another preferred embodiment, the compound stimulates the differentiation of bone cells. Also preferably, the compound is a T1-M protein ligand. More preferably, the ligand is an 18 kd protein expressed in BALB/c-3T3 cells.

In another aspect of the invention, the compound is in solution form.

In yet another aspect, the composition is prepared as a depot.

Also included in the invention is a method of influencing the proliferation and/or differentiation of bone cells. The method comprises administering to the cells a compound capable of modulating the activity of T1-M protein.

In one aspect of this method, modulation of the activity of the T1-M protein is effected by modulating the expression of the T1-M protein. In a preferred embodiment, modulation of the activity of the T1-M protein is effected by the interaction of T1-M protein with the compound. In another preferred embodiment, the activity of T1-M protein is reduced.

In one aspect, the compound is a T1-S-antisense nucleic acid and in another aspect, the compound is a T1-S-sense nucleic acid.

In another aspect, the compound is a T1-M protein inhibitor. In a preferred embodiment, the inhibitor is selected from the group consisting of a monoclonal antibody, a polyclonal antibody and a fragment of an antibody. In another preferred embodiment, the inhibitor is a competitive inhibitor. Preferably, the competitive inhibitor is T1-S protein.

In yet another aspect, the activity of T1-M protein is increased. Preferably, the compound effects a stimulation in the differentiation of the bone cells. Also preferably, the compound is a T1-M ligand. In a preferred embodiment, the ligand is an 18 kD protein expressed in BALB/c-3T3 cells.

The invention also relates to a method of modulating the activity of T1-M protein in vitro. The method comprises administering to a population of bone cells in culture a compound capable of modulating the activity of the T1-M protein. In one preferred embodiment, the activity of the T1-M protein is reduced, whereby proliferation of the bone cells is stimulated. In another preferred embodiment, the activity of the T1-M protein is increased, whereby differentiation of the bone cells is stimulated.

Also included in the invention is a method of treating osteoporosis in a human patient, the method comprising administering to the patient a compound capable of modulating the activity of T1-M protein.

In addition, the invention includes a method of treating osteopetrotic disease in a human patient, the method comprising administering to the patient a compound capable of modulating the activity of T1-M protein.

BRIEF DESCRIPTION OF THE DRAWINGS

FIG. 1A depicts detection of T1 mRNA in total RNA of various K12 T1-antisense subclones with DEX-inducible antisense expression vector in the presence or absence of the synthetic glucocorticoid dexamethasone (DEX, 50 nM) for three hours. 5 kb:T1 mRNA; 2.7 kb: T1-S mRNA. FIG. 1B depicts immunoprecipitation of T1-S protein from the medium of metabolically labeled K12, K12-S2 and K12-AS3 osteosarcoma cells. Precipitation was performed as described in Werenskiold, 1992.

In FIG. 5B, there is presented an image depicting detection of the secreted T1-S protein in media of the 3D cultures of MC3T3, K12, K12-S2 and K12-AS3 cells.

FIG. 6A is a comparison of the growth of the parental line K12 with the subclones K12-AS2, K12-AS3, K12-S1 and K12-S2. The symbols used in FIG. 6A are as shown on the figure. FIGS. 6B and 6C depict the influence of DEX on the growth of K12 (B) and K12-AS2 (C) cells. The symbols used are different from those shown in FIG. 6A and are as follows: -○- preincubation of the cells in medium with 50 nM DEX for three days, proliferation test in the absence of DEX; -●- preincubation of the cells in medium with 50 nM DEX for three days, proliferation test in the presence of 50 nM DEX; -△- preincubation and proliferation test in the absence of DEX; -▲- preincubation in the absence of DEX, proliferation in the presence of 50 nM DEX.

DETAILED DESCRIPTION OF THE INVENTION

Figure 1:
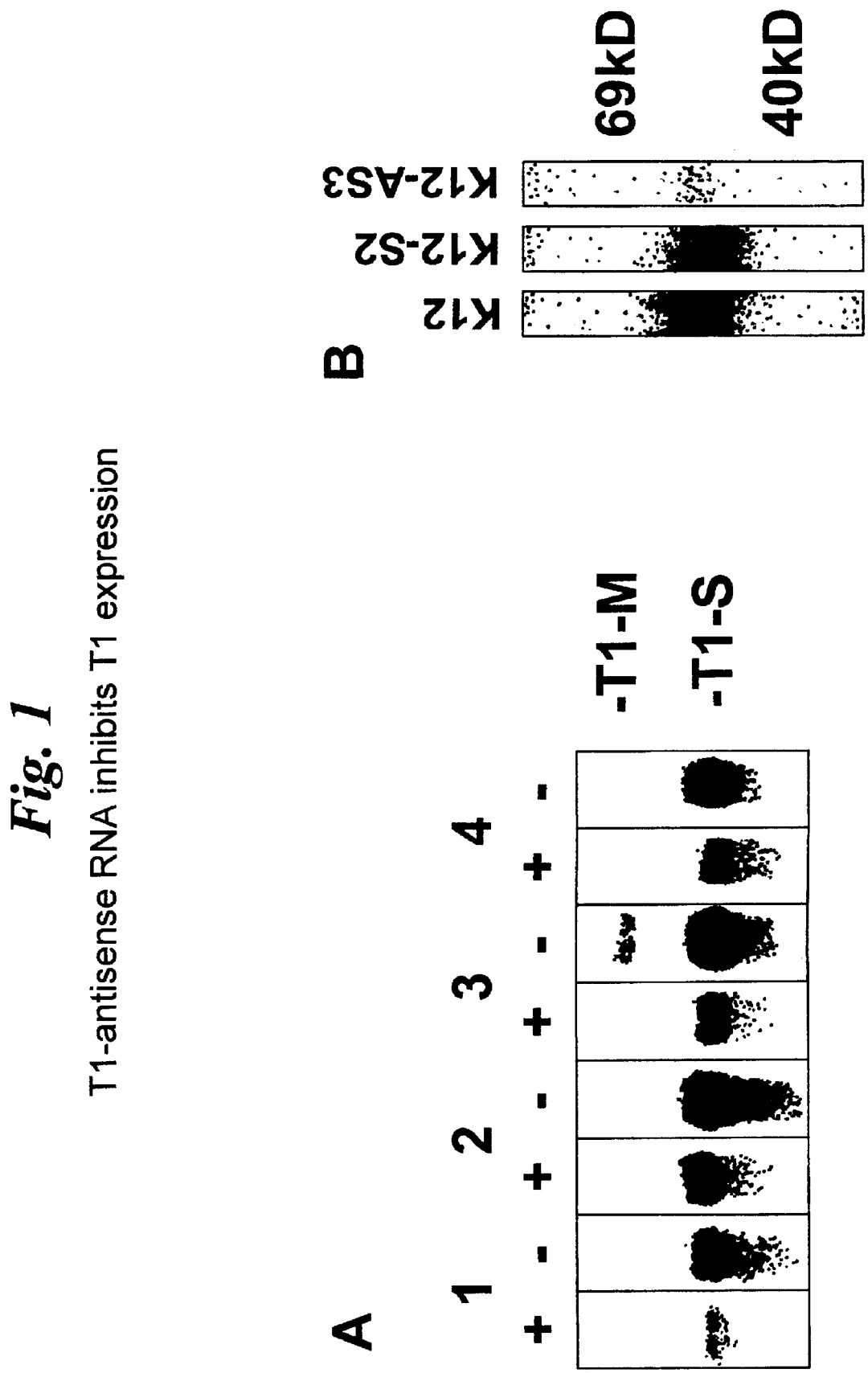
FIG. 1 is a set of images depicting modulation of T1 synthesis in osteosarcoma cells by T1-antisense RNA.

The present invention is related to compositions which contain a compound modulating the activity of T1-M protein, the use of compounds which modulate the activity of T1-M protein, and an in vitro methods for influencing the proliferation and/or differentiation potential of bone cells.

It is an object of the present invention to identify compositions which influence the differentiation or proliferation of bone cells.

According to the invention, this object is achieved through the identification of a composition which contains a compound that can modulate the activity of T1-M protein. Surprisingly enough, it is demonstrated herein that inhibition of the T1-M protein has a proliferation promoting effect on bone cells, whereas activation of the T1-M protein stimulates differentiation of bone cells.

Also according to the present invention, while T1-S is not found in terminally differentiated adult tissues (Rößler, 1995), tumor-associated reexpression of T1-S in osteosarcoma has been observed.

A combined in vitro/in vivo model is described herein which demonstrates the functional significance of strictly regulated T1 synthesis during osteogenesis. A clonal osteosarcoma cell line which can form osseous tissue upon subcutaneous injection into syngeneic mice (Schmidt, 1988) was manipulated by means of recombinant DNA methods to express constitutively enhanced or reduced amounts of T1. A reduction in the osteogenic capability of clonal homogenous cell populations in vitro has shown a substantially autocrine function of T1 and osteogenic cells, which was also apparent in vivo. The results further demonstrate the value of this experimental approach to discriminate the inherent potential of osteogenic cells from the role of exogenous factors provided by the host environment.

Earlier work has pointed to a strictly regulated expression of the T1 gene in osteogenesis. It has been characterized by a high expression of T1 mRNA and T1 protein in early proliferating osteoblasts and the repression of the expression in maturating cells, both in vivo and in vitro. In all of the osteogenic cells that have so far been analyzed, the expression of the 2.7 kb mRNA which codes for T1-S, represents 95 to 99% of the total T1-specific transcripts whereas the 5 kb mRNA, whose translation leads to the T1-M receptor, exists in considerably smaller amounts (Rößler 1995, Werenskiold, 1995). It has been discovered herein that the regulation of the T1 gene expression in osteogenic cells is essential for the initiation of bone differentiation in homogenous cell populations and for the stimulation of proliferation, and, according to the invention, provide compounds which are capable of modulating the activity of the T1-M protein.

"Modulation" in this context means a change in activity caused by the respective compound and embraces both increase and decrease thereof. Activity of the T1 protein designates the capability of the T1 protein for mediating differentiation competence.

Apart from the modulating compound, the composition of the invention optionally contains additives, such as stabilizers, buffer substances, osmotically active substances, etc.

As is demonstrated herein, the activity of the T1-M protein can be changed by modulation at the level of transcription or the level of translation. For instance, the T1-M protein activity can be enhanced at the transcription level by providing additional T1-M mRNA. Translation can be disturbed by intercepting the sense mRNA which is synthesized, e.g., by providing antisense mRNA which renders the sense mRNA no longer available for translation. However, another method of altering the activity of the protein is found at the level of the protein function itself, i.e., by interaction of the T1-M protein with stimulating or inhibiting compounds.

The examples which are presented herein establish that a reduction of the activity of the T1-M protein, no matter how this may be accomplished, enhances the proliferation of bone cells. Such a proliferation-enhancing modulating compound is, for instance, a T1 antisense nucleic acid (DNA or RNA). For instance, the provision of antisense mRNA in T1-M producing cells leads to inhibition of the translation of the T1 mRNA. As a consequence, the concentration of available T1-M receptors on the cell surface decreases, and the cell in question is stimulated into proliferation.

A complete T1 antisense nucleic acid is not imperative for inhibiting translation; experience has shown that it is sufficient to prevent translation by hybridization with an oligonucleotide which is complementary to part of the T1 RNA. Preferred oligonucleotides are DNA oligonucleotides which are complementary to the 5' region of T1 RNA.

In a preferred embodiment, the modulating compound is a DNA oligonucleotide, the sequence of which corresponds to the nucleotides 191–1201 or 277–796 of the cDNA sequence according to Klemenz, 1989.

In a further preferred embodiment, the modulating compound is a T1-S sense nucleic acid, for instance a T1-S mRNA. As shown in the examples, the expression of T1-S mRNA leads to a competition for the ligand, whereby the T1-M protein can also not be activated.

According to a further embodiment, the receptor itself is inhibited. A suitable inhibitor is, for instance, a monoclonal and/or a polyclonal antibody or a functional fragment of such an antibody which blocks the ligand-binding site. Methods for producing such antibodies, both polyclonal and monoclonal types, are well known in the prior art. A precondition therefor is the isolation and substantial purification of the T1 protein, which is already described in Rupp, 1995, for the mouse protein. Following the generation of such antibodies, these are tested for their inhibiting ability. The production of antibody fragments, for instance Fab or $F(ab)_2$ fragments, is also prior art.

The activity of the membrane-bound T1-M protein can further be reduced by competition for the ligand. Modulating compounds which are suited for providing an agent competing for the ligand are, e.g., expression vectors which express T1-S mRNA within the cell. Retroviral vectors or SV40 vectors are preferred for use in human patients. The construction of such vectors is within the scope of expert skill. Hence, a competitive inhibitor is indirectly provided by introducing such a vector into a T1-M producing cell.

Recently, binding proteins have been described that represent possible ligands. In a further embodiment of the invention, the 18 kD protein of BALB/c-3T3 cells as described by Kumar (1995) is used as the modulating compound.

In another embodiment, a competitive inhibitor is directly provided. The T1-S protein itself could, for instance, serve as such an inhibitor. As already stated above, the presence of T1-S protein leads to competition for the ligand and thus to a missing activation of the T1-M protein. As a result, the activity of the T1-M protein is reduced, whereby proliferation of bone cells is stimulated.

Therefore, compositions which contain modulating compounds that reduce the activity of the T1-M protein are well suited for the treatment of osteoporosis patients. Upon application of a corresponding modulating compound cell growth in the treated patient would first start and later be stopped again as soon as the concentration of the modulating compound is decreasing. Possibilities of reducing the proliferation of stimulated bone cells follow also from a reverse approach, i.e., an increase in the activity of the T1-M protein.

The present invention also provides for compositions which serve to enhance the activity of the T1-M protein. As shown in the Examples, an increased activity of the T1-M protein is accompanied by the initiation of a differentiation of bone cells. An increase in the T1-M protein activity can, for instance, be caused by expression vectors which code for the T1-M protein. An increased copy number of the T1-M protein will increase T1-M activity up to depletion of the ligand. As already mentioned above, SV40 or retroviral vectors are primarily suited for use in human patients.

In a preferred embodiment, the modulating compound is a ligand for the T1-M protein. Binding proteins which represent ligands have recently been described (Kumar 1995, Gayle 1996).

The composition of the invention for enhancing the activity of the T1-M protein is suited for treating osteopetrotic diseases.

Compositions of the invention can be administered orally, enterally, parenterally, subcutaneously, intramuscularly or intraperitoneally. They are present in the form of a solution for application by means of injections. Preference is, however, given to applications in which the respectively modulating compound is slowly released, i.e. a depot of the modulating compound is slowly released. A preferred depot material is, e.g., Matrigel® (Becton Dickinson, Heidelberg). Further depot materials are known to one skilled in the art.

According to the invention the modulating compounds contained in the above-described composition are used for producing pharmaceuticals which can influence the proliferation and/or differentiation potential of bone cells. The statements made in connection with the compositions apply analogously.

According to the invention there is further provided a method for the in vitro modulation of the activity of the T1-M protein, wherein bone cells in cell culture are exposed to a compound modulating the activity of the T1-M protein. In response to the selection of the modulating preparations, it is thereby possible to stimulate proliferation of the cell culture in vitro or to activate differentiation. According to the invention bone cells stimulated into proliferation in vitro could optionally be retransplanted into an osteoporosis patient and thus help to alleviate osteoporotic symptoms. Dosages of compounds which are useful for in vivo modulation may vary depending upon any number of factors, including but not limited to, the age and overall health of the individual, the severity of the disease to be treated and the route of administration of the compound.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

The Materials and Methods used in the Examples provided herein are now described.

Cells and Cell Culture Conditions

Establishment of K12 clonal cell line derived from a spontaneous osteosarcoma of a BALB/c mouse, as well as culture conditions, have already been described (Schmidt, 1988).

For three-dimensional cultures, 5×10$^5$ cells were seeded on the upper surface of discs (16 mm diameter) consisting of a three-dimensional network of collagen fibers and were cultured as described (Casser-Befte, 1990).

Proliferation Assays

For proliferation assays, 5×10$^5$ cells/100 µl/well were seeded in microliter plates in triplicate. At the indicated times, 10 µl MTT-PBS solution (5 mg/ml 3-(4,5-dimethylthiazol-2-yl)-2,5-diphenyl-tetrazoliumbromide in phosphate-buffered saline) were added to the cultures. After 4 h incubation at 37° C. the reaction was stopped by addition of 100 µl/well of 10% sodium dodecyl sulfate in 10 mM HCl and plates were incubated at 37° C. for 15 hours. MTT-formazan production was quantitated by measuring OD at 570 nm.

Construction of Expression Vectors

The parental vector pLTR-stp (Jaggi et al., 1986) was linearized with XbaI and BamHI. A 550 bp DNA fragment of the T1-ORF was amplified by using the plasmid pT1.10 (Klemenz, 1989) with the following primer pair: 5'-CGATCTAGAAGTAAATCGTCCTGGGGTC-OH [SEQ ID NO:1] and 5'-CGGGATCCCGGGCAGATCTAAGCTTTGTGAATGATCTGGTGGC-OH [SEQ ID NO:2]. The resulting PCR product was restricted with XbaI and BamHI and inserted into the linearized vector to yield the T1-antisense expression plasmid pLTR-T1. The complete T1-ORF (about 1 kb: position 191-1201, Klemenz et al., 1989) was ligated in the sense orientation into the vector pRc/CMV (Invitrogen Corp., Netherlands; Boshart et al., 1985) to yield the expression plasmid pCMV T1-S.

RNA Extraction and Analysis

Discs of three-dimensional cultures were homogenized in the presence of guanidine isothiocyanate buffer in liquid nitrogen after the culturing period to extract RNA. RNA obtained from single-cell layer cultures, tumor tissue and disc cultures was isolated according to Chirgwin et al., 1979. For Northern analysis, 8–10 µg of total RNA was glyoxylated and separated in 1% agarose gels. The hybridization probes used were derived from plasmids containing cDNA sequences of T1 (Klemenz, 1989), collagen 1 (Chu, 1982), bone-, liver- and kidney-specific alkaline phosphatase (Weiss, 1986), osteocalcin (Ford, 1985) and glyceraldehyde-3-phosphate dehydrogenase.

Protein Analysis

Metabolic labeling and immunoprecipitation of T1-S were performed as already described (Werenskiold, 1992). For detection of T1-S in 3D culture supernatants, 1 ml of medium was incubated in the presence of 50 µl (packed volume) of lentil lectin Sepharose (Sigma, Munich) at 40° C. for 15 hours. The Sepharose beads were washed twice with PBS and bound proteins were solubilized in SDS gel sample buffer. Western blot analysis of the protein extracts was performed as described in (Werenskiold, 1992).

Example 1

Examination of the Impact of T1 Gene Expression on the Differentiation of Osteosarcoma Cells The impact of T1 gene expression on the differentiation of osteosarcoma cells was studied in the osteogenic clonal tumor cell line K12. The cell line is derived from a spontaneously occurring invasive osteosarcoma of a BALB/c mouse and induces the formation of highly differentiated osteosarcomas upon injection in syngeneic mice (Schmidt, 1988). With respect to T1 gene expression, K12 behaves like a typical osteosarcoma cell. Both T1 mRNA and T1 protein are highly expressed in K12 cells.

Example 2

Modulation of T1 Gene Expression in K12 Osteosarcoma Cells

T1-sense or T1-antisense RNA was produced in cells to modulate T1 gene expression in K12 cells. The efficiency of the T1-antisense RNA mediated inhibition of T1 mRNA expression was tested in an inducible system. To this end, K12 cells were transfected with a vector (LTR-T.1.-AS, see above) in which the T1 ORF was inserted in antisense orientation relative to the glucocorticoid-responsive long terminal repeat of mouse mammary tumor virus. Several neomycin-resistant pools and clones of transfectants (K12-

AS) synthesized T1 mRNA in amounts comparable to the parental K12 line in the absence of glucocorticoid. Treatment of K12-AS cells with the glucocorticoid dexamethasone (DEX, 50 nM) considerably reduced the expression of both variants of T1 mRNA. Maximal repression was observed within three hours after addition of DEX (FIG. 1A) and was maintained for several days in the presence of the hormone. To obtain cell lines with permanently altered T1 expression patterns, the complete T1-S ORF was inserted in sense (CMV-T1-S) orientation relative to the constitutive promotor of cytomegalovirus (CMV) in the vector pRc/CMV (see above). Neomycin-resistant cells obtained after transfection of these constructs into K12 cells were assayed for T1 mRNA synthesis. Screening of K12 transfectants containing the LTR-T1-AS construct led to the isolation of the subline K12-AS3, which exhibited constitutively low T1 mRNA expression and did not respond to the addition of hormones. This cell line was used in further experiments to analyze constitutive repression of T1 mRNA synthesis in K12 cells.

Immunoprecipitation of the secreted T1 protein from the supernatant of metabolically labeled cell cultures confirmed the T1 expression levels determined by RNA analysis. As shown in FIG. 1B, K12 and K12-S2 cells secreted high amounts of T1 glycoprotein whereas only minute amounts of the protein could be precipitated from the supernatant of K12-AS3 cells.

Example 3

T1 Modulation Interferes with the Osteogenic Differentiation of Tumors $1 \times 10^6$ cells of the K12, K12-S2, K11-AS3 cell lines were injected into 6 week-old syngeneic BALB/c mice. Tumor growth was monitored and mice were sacrificed when the tumors had reached a mean diameter of 1 cm.

Figure 2:
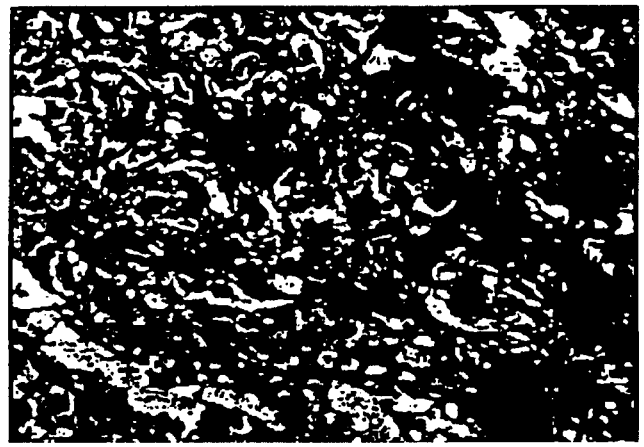
FIG. 2 is a series of images depicting sections of the formalin-fixed and paraffin-embedded decalcified tumors produced by the cell lines described in FIG. 1B were stained according to van Giesson to visualize the formation of bone matrix. K: bone matrix; M: mitosis.
Figure 2:
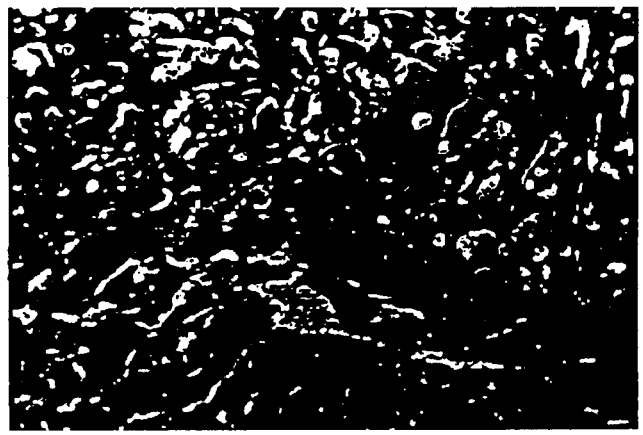
Figure 2:
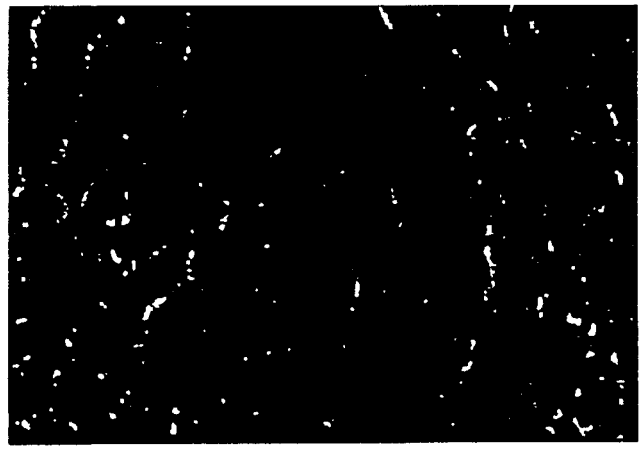

The histological examination of formalin-fixed, paraffin-embedded sections of tumor tissue according to H & E or van Giesson staining demonstrated an ossification of the K12 and K12-S2 tumors. By contrast, tumors of K12-AS3 cells contained pleomorphic cells and a great number of mitoses, but exhibited no ossification (FIG. 2).

Figure 3:
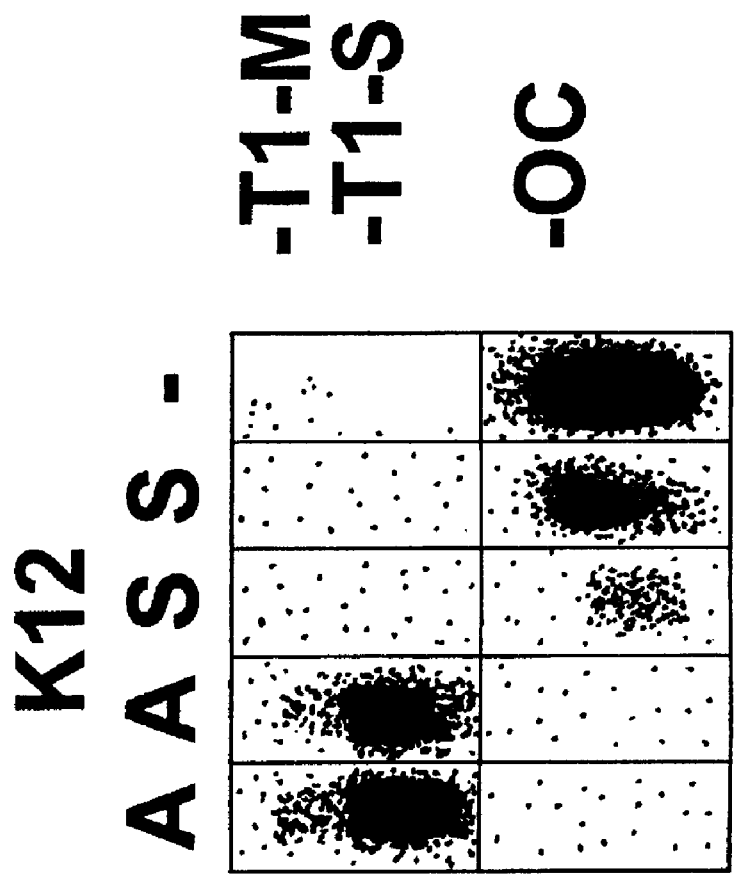
FIG. 3 is an image depicting tumor-associated expression of osteocalcin and T1 mRNAs. The total RNA obtained from frozen tissue (Rößler 1995) of tumors of parental cells(−), T1-sense cells (S) and T1-antisense transfectants (A) of K12 cells, as indicated, were analyzed by means of Northern blot hybridization for expression of osteocalcin (OC-bottom) and T1 mRNA (T1-top). The T1-specific Northern blot contains 2 bands: the upper T1 mRNA is the 5 kb T1 receptor mRNA (Ti-M) while the lower one represents the 2.7 kb T1-S mRNA (T1-S) (Werenskiold, 1995).

These histological findings were confirmed by the analysis of the gene expression in total RNA which had been isolated from two tumors of each cell line. High osteocalcin mRNA levels existed in highly differentiated tumors of K12 and K12-S2 cells, but were not detectable in RNA of the anaplastic tumors of K12-AS3 cells. In contrast to highly differentiated tumors, these had a high T1 mRNA level (FIG. 3).

Example 4

Impact of the Deregulation of T1 Expression on Osteogenic Differentiation in vitro Culturing of osteogenic cells lines for prolonged periods of time within a three dimensional network of collagen type 1 fibers (3D culture) allows for differentiation of the cells in vitro (Casser-Befte, 1996). This model was used to assess the capacity of tumor cell lines for osteogenic differentiation in the absence of exogenous factors.

3D cultures were established with the cell lines K12 and their sublines K12-S2 and K12-AS3 and the non-tumorigenic osteogenic standard cell line MC3T3.

Figure 4:
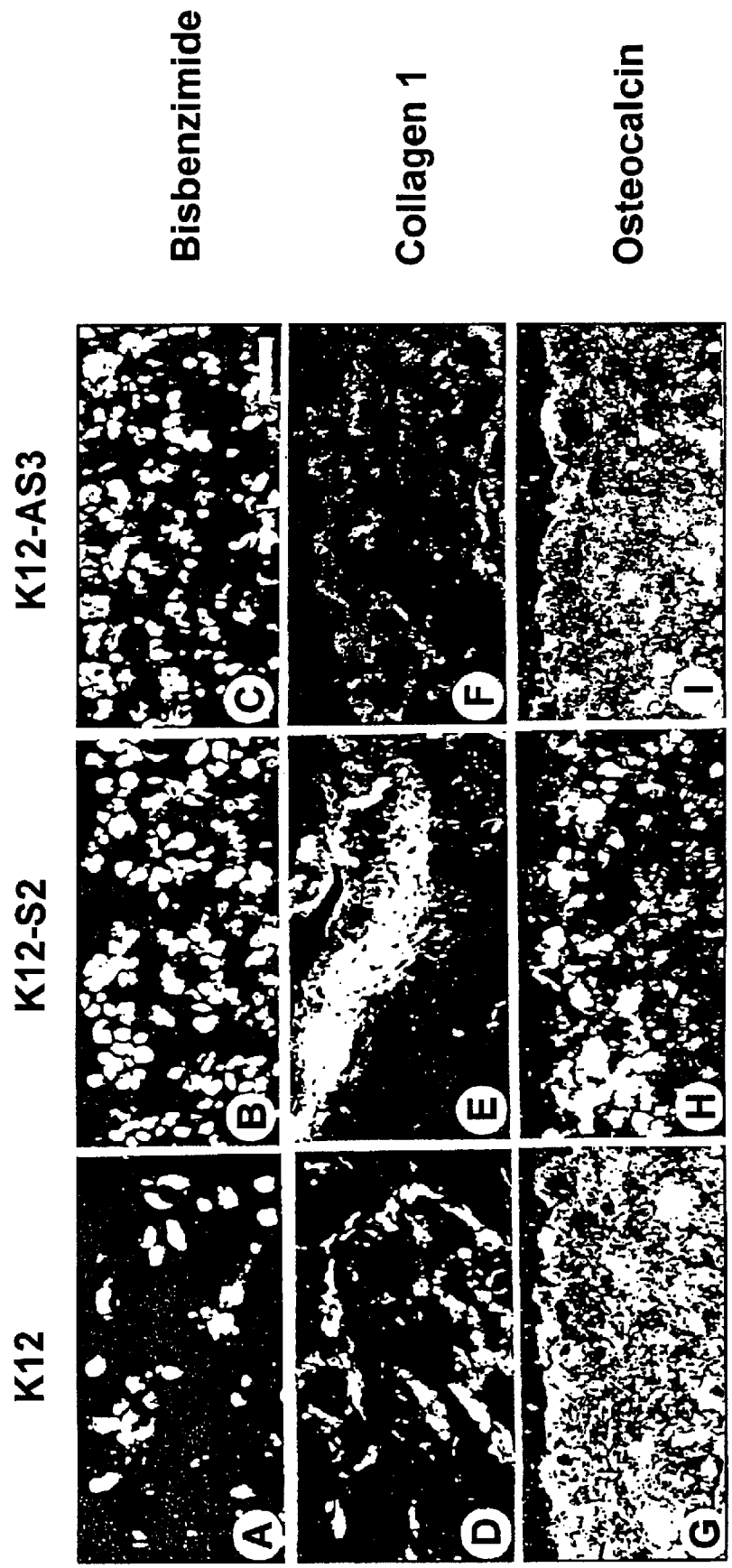
FIG. 4 is a series of images comprising Panels A-I depicting Three dimensional (3D) cultures of K12 cells (Panels A, D and G), K12-S2(Panels B, E and H) and K12-AS3 (Panels C, F and I). Cells were frozen in nitrogen after 30 days of culturing; frozen sections of the cultures were either stained with bisbenzimide (top) (nucleus staining) or with commercially available antibodies against collagen 1 (center) or osteocalcin (bottom).

A histological analysis of frozen sections of the cultures revealed strong proliferation and multilayered growth of all cell lines (see FIG. 4, up to benzimide staining). Synthesis and deposition of the differentiation-specific proteins collagen 1 and osteocalcin could only be detected in cell-rich areas of K12 and MC3T3 cells.

Figure 5:
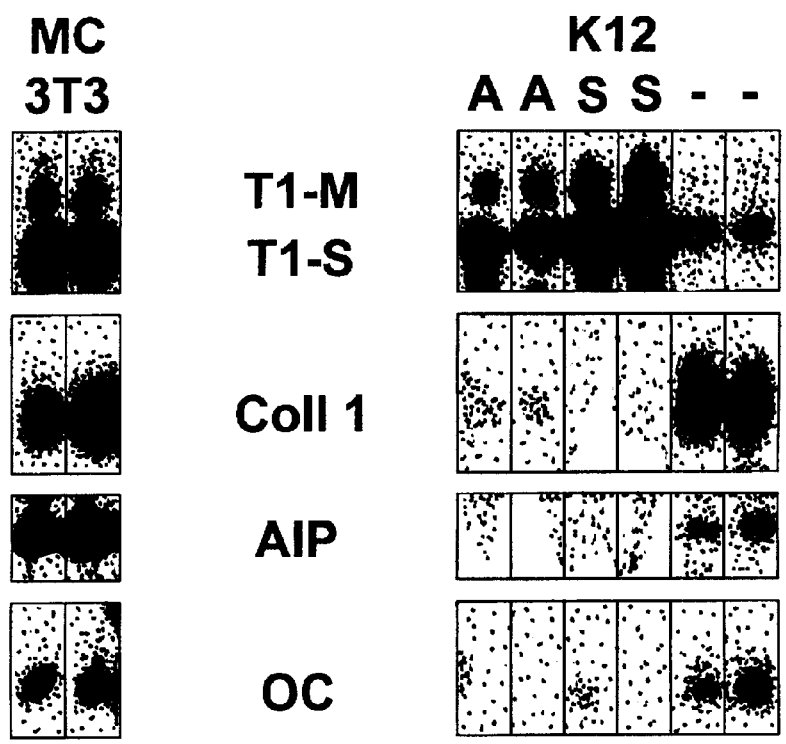
FIG. 5 is a set of images depicting, in FIG. 5A, differential expression of osteogenesis-specific mRNAs in 3D cultures of K12(−), K12-S2(S) and K12-AS3(A) cells as well as MC3T3 cells. Total RNA of two individual cultures of each cell line was analyzed, as described in the description of FIG. 3, for the expression of T1 mRNAs (T1-M, T1-S), collagen type 1 RNA (Coll1), alkaline phosphatase (AIP) and osteocalcin (OC).
Figure 5:
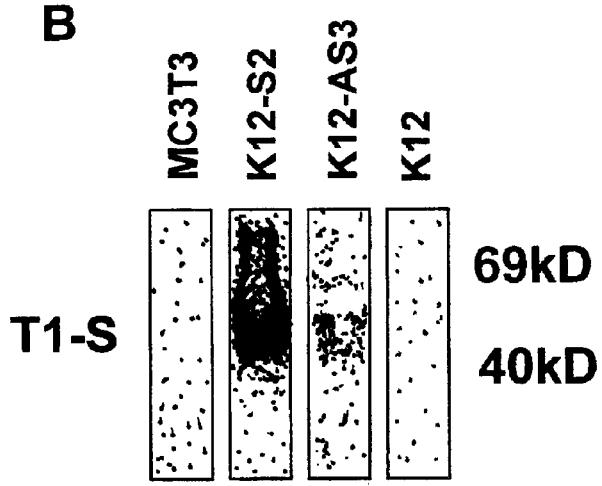

The detection of the expression of osteogenesis-associated genes confirms this finding: Differentiation of the 3D cultures was monitored by analysis of the expression of sequentially expressed osteogenesis-associated genes after four weeks of culture. Similar patterns of expression of osteogenesis-specific genes were observed in 3D cultures of MC3T3 and K12 cells. Collagen type 1 and T1 mRNAs, markers of the early (proliferative) phase of osteogenic differentiation, were expressed only moderately. Alkaline phosphatase mRNA representing the second stage was present in K12 cultures at a reduced level compared to MC3T3 cultures, and osteocalcin, a main expression product during the late osteogenic differentiation, was highly expressed in both cell lines. In K12-S2 and K12-AS3 cultures, mRNA coding for alkaline phosphatase could not be detected and the mRNAs for type 1 collagen and osteocalcin were only faintly visible. By contrast, endogenous T1 mRNA was prominent in K12-S2 cells and to a lower extent in K12-AS3 cells (FIG. 5A).

Accumulation of T1-S protein in the culture medium at the end of the 3D culture period was assayed by Western blot analysis. The medium of K12-S2 contained a high level of T1-S protein, and the medium of K12-AS3 and MC3T3 cells contained a low level, which reflects the amount of mRNA present in the corresponding 3D cultures (FIG. 5B).

Example 5

T1-antisense Mediates Enhanced Proliferation of K12 Cells

Figure 6:
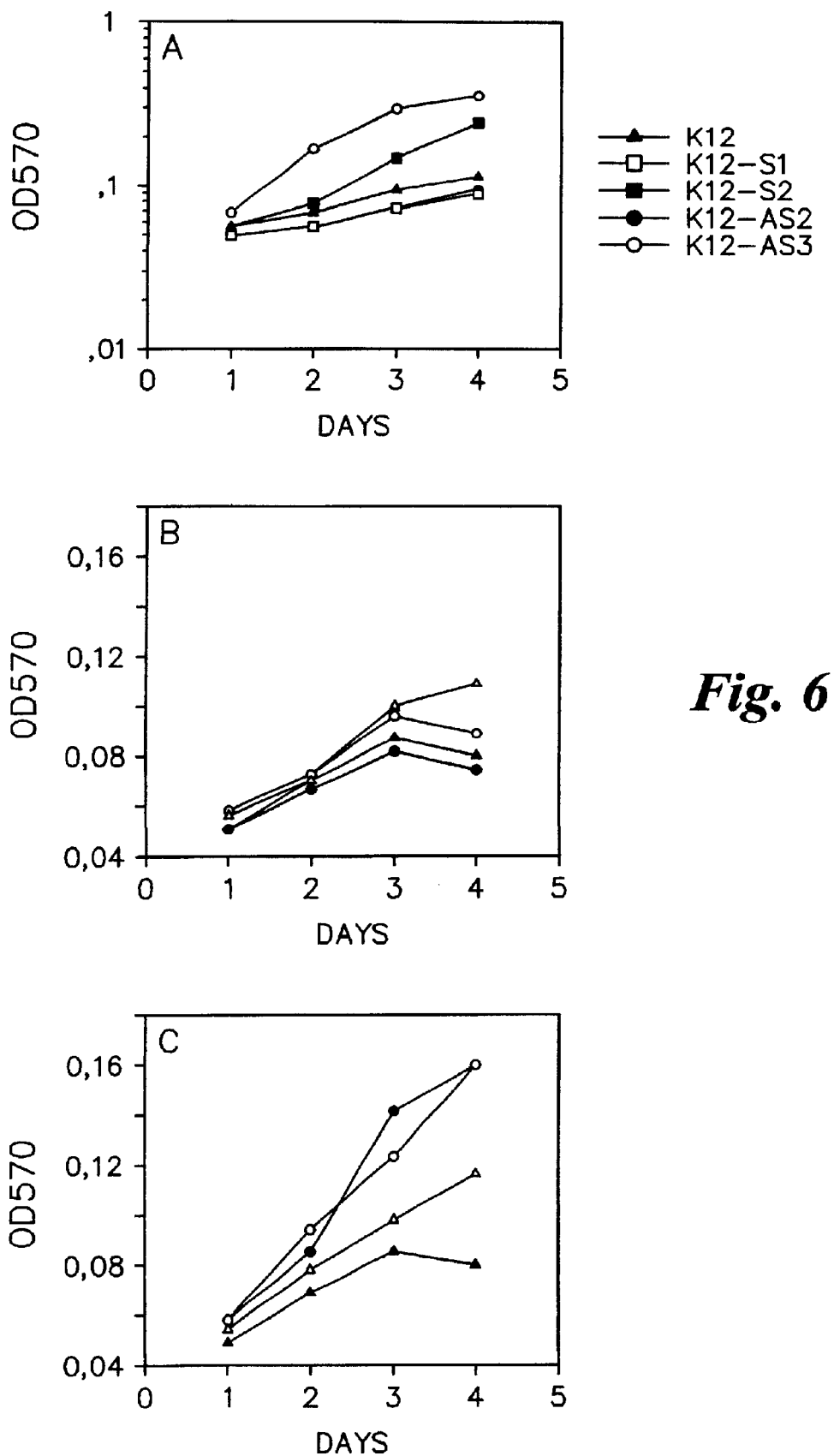
FIG. 6 is a series of graphs depicting the influence of T1-antisense on cell proliferation. Proliferation of the various cell lines was determined by means of MTT test.
Figure 7:
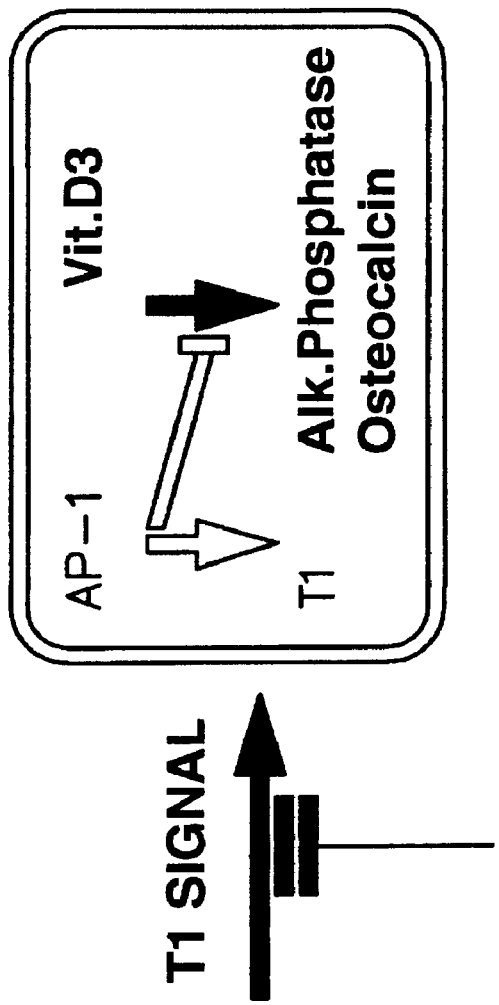
FIG. 7 is an image of a model of T1-receptor function in bone differentiation. In proliferating osteoblasts (OB), high AP-1 activity drives expression of the T1 gene and represses the activation of alkaline phosphatase and osteocalcin genes by vitamin $D_3$. Upon T1 receptor activation, cells undergo a transition to maturing, non-proliferative osteoblasts characterized by low AP-1 and T1 gene activity and high expression of alkaline phosphatase and osteocalcin. T1-antisense expression and the synthesis of competing T1-S block T1 receptor activation and arrest the cells in an undifferentiated, proliferative state.
Figure 7:
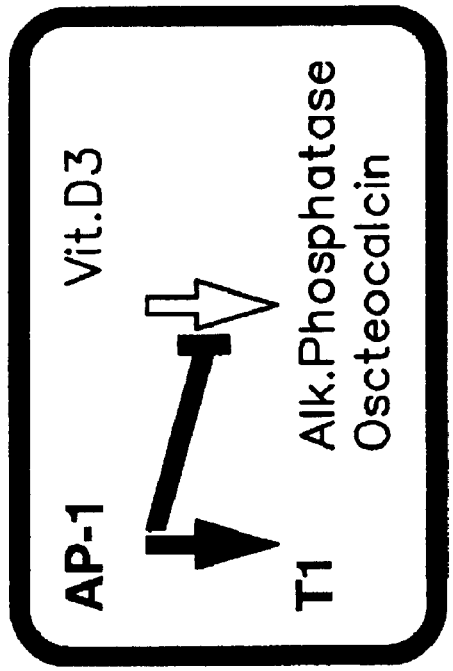

To compare the growth kinetics of various K12 sublines with those of parental lines, $1-10^3$ cells/0.1 ml were seeded in quadruplicate in microliter plates and proliferation was monitored at 24 h intervals for four days using a standard MTT assay (Boehringer Mannheim, FRG). Most K12 sublines (including the inducible LTR-T1-AS lines) exhibited proliferation rates comparable to those of the parental cells (K12-S1, K12-AS) or slightly higher (K12-S2) (FIG. 6A). K12-AS3 cells characterized by a constitutively low T1 expression grew significantly faster than the majority of clones.

A possible role of reduced T1 synthesis in the enhanced proliferation of K12-AS3 cells was investigated in a cell line containing a DEX-inducible T1-antisense construct (K12-AS2). K12, K12-S2 and K12-AS2 were precultured for three days in the presence or absence of 50 nM DEX and subsequently seeded in microliter plates. Proliferation of the cells was tested in the presence or absence of 50 nM DEX, as described above. Both K12 and K12-S2 cells grew with similar kinetics for three days. The presence of DEX during preculturing and/or the assay period reduced the cell density after four days of culture (FIG. 6B). By contrast, preculturing of K12-AS2 cells in the presence of 50 nM DEX significantly enhanced their proliferation both in the absence and presence of DEX through the following assay period. Addition of DEX exclusively during the assay period enhanced final cell density slightly (FIG. 6C).

A Summary of the Data Presented in the Examples

Earlier work demonstrated a strictly regulated expression of the T1 gene in osteogenesis. It was characterized by high expression of T1 mRNA and T1 protein in early, proliferating osteoblasts and repression of the maturing cell both in vivo and in vitro. In all osteogenic cells analyzed so far, the 2.7 kb T1-S mRNA represented 95 to 99% of the T1-specific transcripts whereas the 5 kb mRNA coding for the T1-M receptor was only present at low level (Werenskiold 1995, Rößler 1995). The above described experiments demonstrate that the strict regulation of T1 gene expression in osteogenic cells is essential for the initiation of bone differentiation.

It was demonstrated that the well characterized clonal murine osteosarcoma cell line, K12, was capable of undergoing osteogenic differentiation in vivo and, surprisingly enough, in vitro. The established 3D culture system permitted an osteogenic differentiation of K12 cells to a similar extent as of the well characterized non-tumorigenic osteogenic cell line MM. Thus K12 cells were capable of terminal differentiation in the presence of some exogenous factors provided by the host microenvironment. Therefore, they represent a suitable model to study effects of modulated T1 expression both in homogenous cell populations in the absence of exogenous influences in vitro and after injection into syngeneic animals in vivo. The constitutive expression of T1-sense and T1-antisense RNA proved effective to modulate the pattern of T1 expression pattern in osteosarcoma cells.

Due to the expression of two T1 protein variants, different levels of interaction of T1 modulation with T1 functions have to be considered: 1) T1-sense RNA enforced the constitutive production of the secreted T1 glycoprotein. If present at sufficiently high levels in the cellular environment, this protein acted as a constitutive inhibitor of the T1-M receptor. 2) T1-antisense RNA inhibited the synthesis of both the rare T1-M receptor (encoded by the 5 kb mRNA) and of the abundant secretary T1-S protein (encoded by the 2.7 kb mRNA) (FIG. 1). The antisense-mediated inhibition of T1-S secretion was complementary to the effect of the T1-sense construct. However, inhibition of T1-M receptor synthesis acted at a different level and may interfere directly with the T1 receptor signal chain in T1-antisense expressing cells. All of these levels of interference with cell function are apparently involved in the results described above.

T1-antisense Effects

The inhibition of T1 synthesis affected growth and differentiation in the K12 cell line. K12-AS cells grew faster in culture. In cells with inducible T1-antisense expression, growth enhancement first required a downregulation of T1 synthesis prior to the analysis of proliferation. This result is in sharp contrast to the observed fast and efficient antisense-induced inhibition of T1-S synthesis. It indicates that a downregulation of the expression of the cellular T1-M receptor rather than of the secreted T1-S protein conditions the cells for faster proliferation.

Further, T1 antisense abrogated the osteogenic capability of K12 cells in vitro and in vivo. This block in differentiation could not be overcome in the presence of exogenous factors which stimulate terminal differentiation of parental K12 cells. Thus, the T1 antisense mediated inhibition of osteogenic differentiation is an inherent defect of K12AS cells, most likely attributable to the T1-M receptor.

T1-sense Effects

Constitutive synthesis of T1-S in K12-S cells displayed differential effects in the experimental systems. No effect was observed in proliferating monolayer cultures, where the secreted protein was diluted in the supernatant. However, in 3D cultures, constitutive T1-S secretion effectively inhibited osteogenesis. This may be due to an increased local concentration of secreted T1-S in a differentiation-permissive microenvironment due to a high local cell density. In experimental tumors, the inhibitory activity of constitutively secreted T1-S was overcome, probably by its sequestration in the host tissues.

T1 Function in Osteogenic Cells

The results obtained with K12 cells are compatible with the following interpretation: K12 cells were immortalized in an early, differentiation-competent state characterized by high T1 gene activity. Osteogenic cells in the early, proliferative state of differentiation express both secretary T1-S and the T1-M receptor. Inhibition of T1 receptor signal chain by T1-antisense RNA in these cells completely blocked osteogenic differentiation at this early stage whereas it enhanced the proliferation in immature cells. This finding suggests that a T1 receptor mediated signal is essential to maintain a differentiation competent osteogenic state (accompanied by a lower proliferation rate). Interference with T1-receptor signal chain by competing extracellular T1-S protein also inhibited osteogenic differentiation. However, T1-S mediated inhibition was more sensitive to the experimental conditions, indicating the requirement for high local concentrations of the protein.

At the molecular level, the inhibition of differentiation was reflected by the absence of osteogenesis-specific transcripts encoding alkaline phosphatase and osteocalcin. In fact, both the 3D cultures and the tumors support the notion that expression of T1 and osteocalcin genes are mutually exclusive. A possible explanation for this phenomenon is in the promotor structure of the responsive genes. T1 gene expression is activated by the fos/jun transcription factor (AP-1, Trub 1995), whereas vitamin D dependent activation of the osteocalcin gene promotor may be blocked by binding of AP-1 complexes with the overlapping vitamin D responsive element (Schüle 1995, Owen 1990, 1993). Since interference with T1 receptor signal chain promotes sustained cell proliferation and thus continued presence of the fos transcription factor, the vitamin D dependent promoters of differentiation-specific genes remain blocked.

In summary, the data presented herein suggest that the T1-M receptor in immature osteogenic cells supplies an essential signal for the establishment of a differentiation competent state which is connected with low proliferation. Inhibition of its function enhances cell growth at the expense of differentiation competence. This interpretation implies an autocrine production of the T1 ligand in immature osteogenic cells. The demonstration of a possible T1 ligand in 3T3 fibroblasts having a similar T1 expression pattern supports this assumption.

REFERENCES

Boshart et al., 1985, Cell 41, 521–530.
Casser-Bette, M.; Murray, A. B.; Closs, E. I.; Erfle, V., and Schmidt, J. (1990) Calcif. Tissue Int., 46, 46–56.
Chirgwin, J. M.; Przybyla, A. E.; McDonald, R. J., and Rutter, W. J. (1979) Biochemistry, 18, 5294–5299.
Chu, M. L.; Myers, J. C.; Bernard, M. P.; Ding, J. F., and Ramirez, F. (1982) Nuc. Acids Res., 10, 5925–5934.
Fort, P.; Piechacyzk, M.; El Sabrouty, S.; Dani, C.; Jeanteur, P., and Blanchard, J. M (1985) Nuc. Acids Res., 13–327–334.
Gayle, M. A.; Slack, J. L., Bonnert, T. P.; Renshaw, B. R.; Sonoda, G.; Taguchi, T.; Testa, J. R.; Dower, S. K., and Sims, J. E. (1996) J. Biol. Chem. 271, 5784–5789
Jaggi, R., Salmons, B., Müller, R. and Groner, B., 1986, EMBO J 5, 2609–2616.
Klemenz, R.; Hoffman, S., and Werenskiold, A. K. (1989) Proc. NatL Acad. Sci. USA, 86, 5708–5712.

Kumar, S.; Minnich, M. D., and Young, P. R. (1995) J. Biol. Chem., 270, 27905–27913.

Owen, T. A.; Aronow, M.; Shalhoub, V.; Barone, L. M.; Wilming, L; Tassinari, M. S.; Kennedy, M. B.; Pockwinse, S.; Lian, J. B., and Stein, G. S. (1990) J. Cell. Physiol., 143, 420–430.

Owen, T. A.; Bortell, R.; Shaloub, V.; Heinrichs, A.; Szein, J. A.; Stein, G. S., and Lian, J. B. (1993) Proc. NatL Acad. Sci. USA, 90, 1503–1507.

Rößler, U.; Thomassen, E.; Hutner L.; Baier, S.; Danescu, J.; and Werenskiold, A. K. (1995) Dev. Biol, 168, 86–97.

Rupp, B.; Rößler, U.; Löwel, M., and Werenskiold, A. K. (1995) Biochem. Biophys. Res. Corn., 216, 595–601.

Schmidt, J.; Strauβ, P. G.; Schön, A.; Luz, A.; Murray, A. B.; Melchiori, A.; Aresu, O., and Erfle, V. (1988) Differentiation, 39, 151–160.

Schüle, R.; Umesono, K.; Mangelsdorf, D. J.; Bolado, J. and Evans, M. (1990) Cell, 61, 497–504.

Thomassen, E.; Kothny, G.; Haas, S.; Danescu, J.; Hültner, L.; Dörmer, P., and Werenskiold, A. K. (1995) Cell Growth Differ., 6, 178–184.

Tominaga, S.; Yokota, T.; Yanagisawa, K.; Tsukamoto, T.; Takagi, T., and Tetsuka, T. (1992) Biochim. Biophys. Acta, 1171, 215–218.

Trueb, T.; Kalousek, M. B; Fröhli, E., and Klemenz, R. (1994) Proc. Nati. Acad. Sci. USA, 91, 3896–3900.

Weiss, M. J.; Henthorn. P. S.; Lafferty, M. A.; Slaughter, C.; Raducha, M., and Harris, H. (1986) Proc. Natl. Acad. Sci. USA, 83, 7182–7186.

Werenskiold, A. K. (1992) Eur. J. Biochem., 204, 1041–1047.

Werenskiold, A. K.; Rößler, U.; Löwel, M.; Schmidt, J.; Heermeier, K.; Spanner, M., and Strauβ, P. G. (1995) Cell Growth Differ., 6, 171–177.

Yanagisawa, K.; Takagi, T.; Tsukamoto, T.; Tetsuka, T., and Tominaga, S. (1993) FEBS Lett., 318, 83–87.

The disclosures of each and every publication, patent, and patent application cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of assessing whether a composition is useful for modulating at least one of bone cell proliferation and bone cell differentiation, the method comprising comparing
   a) expression of T1-M protein by a test cell maintained in the presence of the composition; and
   b) expression of T1-M protein by a test cell maintained in the absence of the composition, whereby a difference in expression of T1-M protein between the test cells is an indication that the composition is useful for modulating at least one of bone cell proliferation and bone cell differentiation.

2. The method of claim 1, wherein the composition comprises a compound that binds specifically with a T1 mRNA or its complement.

3. The method of claim 2, wherein the compound is a nucleic acid.

4. The method of claim 3, wherein the nucleic acid is selected from the group consisting of a T1-S antisense nucleic acid and a T1-M antisense nucleic acid.

5. The method of claim 1, wherein the test cells are K12 cells.

6. The method of claim 1, wherein the test cells are manipulated to express constitutively enhanced or reduced amounts of T1.

7. A method of assessing whether a composition is useful for enhancing bone cell proliferation, the method comprising comparing proliferation of test cells which comprise an exogenous expression vector encoding T1 protein and which express T1-M protein a) in the presence of the composition and b) in the absence of the composition, whereby enhanced proliferation of the test cells in the presence of the composition, relative to proliferation of the test cells in the absence of the composition, is an indication that the composition is useful for enhancing bone cell proliferation.

8. The method of claim 7, wherein the test cells are K12 cells.

9. A method of assessing whether a composition is useful for enhancing bone cell differentiation, the method comprising comparing proliferation of test cells which comprise an exogenous expression vector encoding T1 protein and which express T1-M protein a) in the presence of the composition and b) in the absence of the composition, whereby decreased proliferation of the test cells in the presence of the composition, relative to proliferation of the test cells in the absence of the composition, is an indication that the composition is useful for enhancing bone cell differentiation.

10. The method of claim 9, wherein the test cells are K12 cells.

\* \* \* \* \*